United States Patent
Rizoiu et al.

(10) Patent No.: US 7,270,657 B2
(45) Date of Patent: Sep. 18, 2007

(54) RADIATION EMITTING APPARATUS WITH SPATIALLY CONTROLLABLE OUTPUT ENERGY DISTRIBUTIONS

(75) Inventors: Ioana M. Rizoiu, San Clemente, CA (US); Dmitri Boutsoussov, Dana Point, CA (US); Jeffrey W. Jones, Ropertson, WY (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

(21) Appl. No.: 11/074,452

(22) Filed: Mar. 8, 2005

(65) Prior Publication Data

US 2006/0204203 A1 Sep. 14, 2006

Related U.S. Application Data

(63) Continuation of application No. 10/229,374, filed on Aug. 26, 2002, now Pat. No. 6,942,658.

(60) Provisional application No. 60/314,858, filed on Aug. 24, 2001.

(51) Int. Cl.
 *A61B 18/18* (2006.01)

(52) U.S. Cl. .............................. 606/16; 606/17; 606/88
(58) Field of Classification Search ........ 385/115–117, 385/146–147, 901; 362/296, 298; 606/13–17, 606/88–91; 607/88–91, 94; 600/247, 248
See application file for complete search history.

(56) References Cited

U.S. PATENT DOCUMENTS

| | | | | |
|---|---|---|---|---|
| 4,929,246 | A * | 5/1990 | Sinofsky | 606/8 |
| 6,383,176 | B1 * | 5/2002 | Connors et al. | 606/9 |
| 6,530,921 | B1 * | 3/2003 | Maki | 606/15 |
| 6,942,658 | B1 * | 9/2005 | Rizoiu et al. | 606/16 |

* cited by examiner

*Primary Examiner*—Quyen Leung
(74) *Attorney, Agent, or Firm*—Stout, Uxa, Buyan & Mullins, LLP

(57) ABSTRACT

A laser handpiece is disclosed, including a fiber optic end having a non-cylindrical shape and further including a reflector surrounding a portion of the fiber optic end. The reflector is shaped to direct laser energy emitted from the fiber optic end in a direction away from the laser handpiece and toward a treatment site.

11 Claims, 2 Drawing Sheets

RADIATION EMITTING APPARATUS WITH SPATIALLY CONTROLLABLE OUTPUT ENERGY DISTRIBUTIONS

CROS-REFERENCE TO RELATED APPLICATIONS

This application is a continuation of U.S. application Ser. No. 10/229,374, filed Aug. 26, 2002 now U.S. Pat. No. 6,942,658 and entitled RADIATION EMITTING APPARATUS WITH SPATIALLY CONTROLLABLE OUTPUT ENERGY DISTRIBUTIONS, which claims the benefit of U.S. Provisional Application No. 60/314,858, filed Aug. 24, 2001, the entire contents of which are incorporated herein by reference.

BACKGROUND OF THE INVENTION

1. Field of the Invention

The present invention relates generally to medical devices and, more particularly, to laser handpieces.

2. Description of Related Art

Radiation delivery systems are typically used to transport electromagnetic energy from electromagnetic energy sources to treatment sites. One common radiation delivery system can comprise a cylindrically-shaped fiber optic tip from which electromagnetic energy is emitted in a direction toward the treatment site.

In certain applications, radiation delivery systems can be engineered to generate predetermined beam shapes and spatial energy distributions. The energy distribution of a simple delivery system, comprising a fiber optic tip, can be described as having a circular illumination area, with a so-called Gaussian distribution of beam intensities being spatially distributed within the illumination area. For instance, the illumination area from a fiber optic tip can comprise a central high-intensity area or "hot spot" surrounded by peripheral areas of lower intensity.

Regarding energy distributions, some beam profiling applications can require or would be optimized with radiation delivery systems capable of generating illumination areas of relatively uniform density across parts or all of the illumination area. Moreover, it may also be desirable to generate non-circular illumination areas, or to generate electromagnetic radiation having predetermined energy distributions across a non-planar illumination area. Use of laser radiation having a relatively uniform power distribution over a particularly shaped area can be a practical task for multiple medical applications. In seeking to generate predetermined energy distributions, prior-art systems have implemented relatively complex optical schemes with multiple optical elements, which systems can be relatively large and/or inefficient. A prior-art system may comprise, for example, a relatively large length, e.g., about 100 mm to 150 mm, measured from the trunk fiber to the output end of the system and measured in a direction normal to the target. Regarding efficiency, implementation of a diffuser in front of a prior-art fiber optic end together with a mirror reflector may not eliminate the "hot spot" problem and would introduce losses of laser power, which configuration can undesirably result an efficiency as low as about 50%.

SUMMARY OF THE INVENTION

The present invention provides optical arrangements and relatively compact medical laser instruments to deliver electromagnetic radiation to treatment sites with relatively uniform power distributions over relatively wide illumination areas. The illumination areas may comprise planar surfaces in which case uniform power densities are generated throughout a cross-sectional area of the impinging radiation where the radiation intersects the treatment site; or the illumination areas may comprise non-planar surfaces, such as arched surfaces, in which case uniform power densities are generated to be relatively evenly distributed on the non-planer treatment site. The electromagnetic energy can comprise laser radiation, and the treatment site can comprise tissue to be treated.

In accordance with one aspect of the present invention, a laser handpiece includes a fiber optic end, which comprises a non-cylindrical shape and which is disposed within a reflector that is shaped to direct laser energy emitted from the fiber optic end in a direction away from the laser handpiece and toward a treatment site. The fiber optic end may have a spherical, conical, chiseled or other light dispersing shape, so long as, when coupled with the reflector, the resulting emitted radiation is a relatively uniform power density across a predetermined treatment site.

The combination of the shaped fiber optic end and the reflector operate together to generate radiation having a relatively uniform power density across an illumination area. The illumination area may have a substantially planar or non-planar topography.

In accordance with another aspect of the invention, the shaping of the fiber optic end to a non-cylindrical shape in conjunction with placement of the shaped reflector around the fiber optic end, can be performed to create a desirable distribution of laser power over the targeting area, wherein the targeting area may comprise, for example, a ring or outline shape, a gradual distribution, or a uniform distribution of spatially-distributed energy. A relatively small number of optical components is used and losses of optical power are minimal.

The various embodiments of the present invention may include or address one or more of the following objectives. One objective is to provide a fiber optic having a shaped fiber optic end (i.e., a fiber optic end not consisting only of a planar surface orthogonal to the fiber optic axis) for delivery of electromagnetic radiation, wherein electromagnetic radiation exiting the fiber optic end is not concentrated along the fiber optic axis. Another objective is to provide a fiber optic end having an emission characteristic whereby electromagnetic radiation exiting the fiber optic end is relatively weak along the fiber optic axis. A reflector is provided to redirect a portion of the electromagnetic radiation back toward a direction the fiber optic axis Yet another object is to provide a fiber optic end wherein all waveguide modes experience total internal reflection on a first surface of the fiber optic end and go out through an opposite surface of the fiber optic end. The fiber optic end can be a cone. Another objective is to provide a fiber optic end in proximity to a highly reflective mirror, which is formed to illuminate the target area with a specific illumination-area shape and/or distribution required for particular medical application. The shape can be non-circular and the distribution can be uniform as measured on a non-planar surface, which can comprise, for example, an arched surface. Yet another objective is to provide a apparatus for providing uniform distributions of power density across an illumination area, with optical losses less than 10% and/or with a minimal number of optical components. Another objective is to provide an apparatus with a relatively short length, measured in a direction normal to the target.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

DETAILED DESCRIPTION OF THE PRESENT INVENTION

Figure 1:
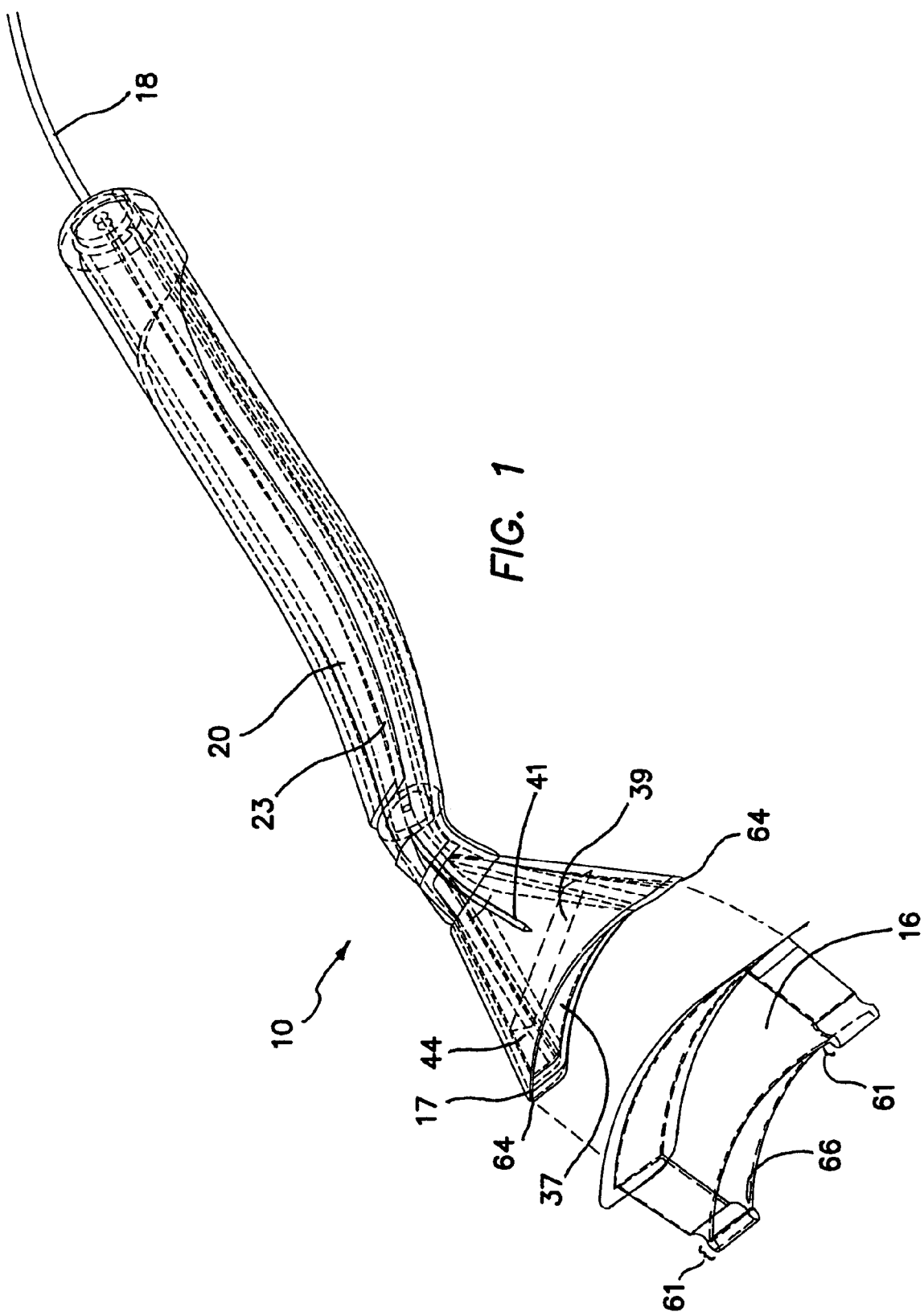
FIG. 1 shows a radiation emitting apparatus designed for uniform illumination of an arched rectangular surface.

Reference will now be made in detail to certain embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

Referring more particularly to the drawings, FIG. 1 shows an exemplary embodiment of a radiation emitting apparatus 10 which is constructed to emit electromagnetic radiation in a nonconcentrically-focused manner, relative to the output from a cylindrically-shaped fiber optic end (i.e., a truncated fiber end). The output radiation 12 (FIG. 3, infra) is engineered to have a spatial energy distribution which differs from the spatial energy distribution of a conventional truncated fiber end. More particularly, in accordance with an aspect of the present invention, the radiation emitting apparatus 10 is constructed to generate output radiation 12 having a spatial energy distribution with one or more energy concentrations or peaks located in areas other than a center of the spatial energy distribution. The center of the spatial energy distribution can be defined as an area aligned with (or intersecting) an optical fiber axis of the apparatus or an area aligned with (or intersecting) an average direction of propagation of the output radiation 12. According to one aspect, the center of the spatial energy distribution can be defined as a central part of a cross-section of the output radiation taken in a direction orthogonal to the direction of propagation of the output radiation.

The output radiation in one embodiment has a spatial energy distribution which is relatively uniform across a geometric surface intersecting the output radiation. The geometric surface can be for example orthogonally disposed relative to the output radiation. In the illustrated embodiment, the geometric surface is curved, but in other embodiments the geometric surface can be planar. A curved geometric surface can approximate a curved surface of the treatment site, so that when the treatment site is aligned with the curved geometric surface the treatment site is irradiated uniformly with about the same energy at all of the points on the treatment site. The treatment site can comprise, for example, a part of the body, such as a row of teeth, an elbow, a wrist, or a portion of the jaw to be treated for TMJ, wherein the curved geometrical surface is designed to follow the envelope of the anatomical area requiring treatment.

In the illustrated embodiment, a uniform power distribution is generated over the area of a curved geometrical surface, which has a rectangular boundary of for example about 35 mm by about 7 mm. In this embodiment, the output radiation is applied uniformly within the rectangular boundary. The treatment site in the illustrated embodiment comprises the upper arch of teeth in the mouth, whereby the curved geometric surface defining the light emitting area of the apparatus is shaped as an arched rectangular surface 14 (FIG. 3, infra) to follow the anatomy of the upper arch of teeth. The radiation emitting apparatus 10 may also be used, for example, for whitening teeth, caries prevention, caries detection (in combination with filtered eyeglasses to visualize and detect emitted fluorescent light), desensitizing teeth and composite curing (restorations, laminates, brackets for braces).

The radiation emitting apparatus 10 is shown in the form of a handpiece, which comprises an ergonomic design, a window 37 and an optional diffuser 39. Placement of the optional diffuser 39, which can comprise a Ground Glass plate with #1500 grade finish from OptoSigma Inc., CA, between the shaped fiber optic end 41 and output surface, may not provide a visible improvement of the power uniformity, and may decrease overall power by 5-8%. However, in constructions wherein the shaped fiber optic end 41 is positioned at a non-optimal distance, the diffuser 39 may slightly improve the uniformity of power distribution.

A optional protective cap 16 cover may be attached to the radiation emitting apparatus 10. This cap may have 'feet' that provide the required distance between the apparatus and the target (e.g., teeth) surfaces to distribute the energy evenly. In the illustrated embodiment, the arched surface 14 is spaced about 1 mm from the teeth by the spacers 61, when the cap 16 is properly placed over the funnel shell 17 so that the ends 64 of the funnel shell 17 snap into the corners 66 of the cap 16. In another embodiment, the funnel shell 17 is omitted and the cap 16 is placed over the shaped reflector 44 so that the ends of the reflector snap into the corners 66 of the cap. The cap 16, which is preferably substantially transparent to the output radiation, can be disposable and can comprise a snap-on construction to facilitate rapid attachment and removal thereof from an funnel shell 17. The cap 16 can further ensure clean surfaces of the applied parts.

A fiberoptic cable 18 is placed in a handpiece handle 20 of the radiation emitting apparatus 10, wherein as presently embodied the fiberoptic cable 18 comprises either metal or a built-in metal tubing 23 to attenuate any possible fiber optic damage. Fiber optic is placed inside the fiberoptic cable 18, which is fixed both on an electromagnetic energy source side (not shown) and in the radiation emitting apparatus 10.

Electromagnetic energy can be supplied at wavelengths from about 0.4 μm to about 11 μm, and more preferably from about 0.4 μm to about 3 μm, from a light source such as a plasma arc lamp, a LED, or a laser having a continuous wave (CW) or pulsed mode of operation. In one embodiment, the electromagnetic energy is laser radiation from a semiconductor diode laser source, delivering up to 10 W CW at an 815+/−10 nm wavelength. For a rectangular area of 35 mm by 7 mm, the energy density is about 3 to 4 W/cm$^2$.

The radiation emitting apparatus 10 comprises a shaped fiber optic end 41, which comprises a non-cylindrical shape and which is disposed within a "beam homogenizing" shaped reflector 44 that is shaped to direct laser energy emitted from the fiber optic end in a direction away from the laser handpiece and toward a treatment site. As presently embodied, the shaped reflector 44 comprises a relatively short length, measured in a direction normal to the target. More particularly, as presently embodied the length, measured in a direction of and along the "straight path" shown in FIG. 3, infra, of the shaped reflector 44 was set at a relatively small length of about 25 mm between the proximal end of the reflector and the distal end of the reflector 17 mm on the arched surface 14.

The fiber optic end may have a spherical, conical, chiseled or other light-intensity altering (e.g., dispersing) shape. In accordance with an aspect of the present invention, the shaped fiber optic end is formed so as, when combined with a reflector (e.g., 44), to provide a relatively uniform power density across the topography of a predetermined treatment site.

The combination of the shaped fiber optic end 41 and the shaped reflector 44 operate together to generate radiation having a relatively uniform power density across the arched surface 14. The shaping of the fiber optic end 41 to a non-cylindrical shape in combination with placement of the shaped reflector 44 around the fiber optic end 41, can be performed to efficiently create a desirable distribution of laser power over the arched surface 14. In other embodiments, shaped fiber optic ends can be combined with reflectors to generate distributions of energy on a curved geometrical surface in the form of, for example, one or more of an outline or ring shape, a gradual transition, or a uniform distribution.

In the illustrated embodiment, to attenuate or avoid undesirable phenomena such as masking and power losses, the shaped fiber optic end 41 is polished to a conical shape. This shape in combination with the chosen shape of the reflector can facilitate generation of a relatively uniform power density across the arched surface 14 at an efficiency of about 90%.

Figure 2:
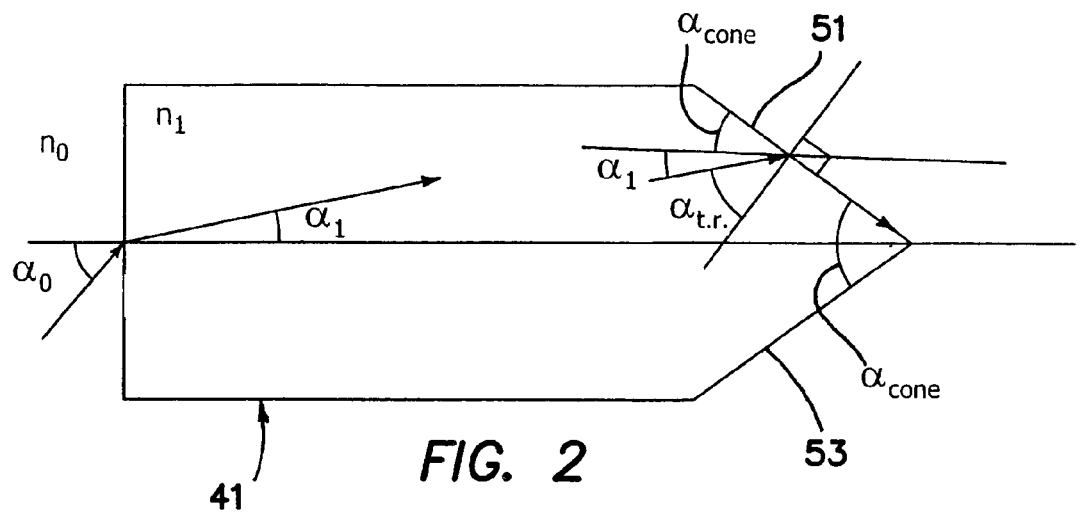
FIG. 2 shows use of the Snell's Refraction Law to calculate cone angle of a fiber optic end of the radiation emitting apparatus.

Turning to FIG. 2, the full angle at the output end of the shaped fiber optic end 44 can be in the range from 10 to 170 degrees, and more preferably between 50 and 100 degrees. In the illustrated embodiment, the fiber optic end 44 comprises a conical shape that tapers in an output direction of propagation. The fiber optic can be a single fiber optic or a bundle. The fiber optic can have a diameter between 50 and 2000 μm, and can have a numerical aperture (N.A.) depending on the material. The fiber optic can be made of silica or other materials, such as sapphire, or other materials disclosed in U.S. Pat. No. 5,741,247, the contents of which are incorporate by reference herein, and can also comprise a hollow waveguide. In one embodiment, for example, the fiber optic comprises a 600 μm core diameter, a numerical aperture of 0.39, an acceptance angle, alphal, of 15.6 degrees, and a full cone angle of 60° to 62°.

The full cone angle can be determined using, for example, Snell's Law of Refraction for all waveguide modes to experience total internal reflection on at least one of the tapered surfaces of the output end of the cone before exiting through the output end of the cone. More particularly, in the illustrated embodiment, the cone comprises a first tapered surface 51 and an opposing second tapered surface 53. According to an embodiment of the present invention in which total internal reflection occurs, all light striking the first tapered surface 51 is reflected toward and exits through the second tapered surface 53. Using the equations shown in FIG. 2, the angle for total internal reflection, alpha t.r., is determined to be 43.6 degrees for an embodiment wherein refractive indices $n_0$ and $n_1$ are 1.0 and 1.45, respectively, corresponding to an implementation of a quartz fiber cone transmitting into air. The total cone angle is calculated in the example to be 61.6 degrees. Although the full cone angle in the illustrated embodiment is selected to facilitate total internal reflection, modified embodiments may be constructed wherein the internal reflection (i.e., reflection off of a first tapered surface of the cone, or the percentage of reflection from light first striking any tapered surface of the cone) is 90% or greater. In still other embodiments, a total cone angle can be constructed to provide for an internal reflection of at least 75%.

The cone angle of the shaped fiber optic end 41, the position of the fiber optic inside the shaped (e.g., tapered) reflector and the angles of the side walls of the mirror reflector are interdependent and in the illustrated example are calculated to provide a very uniform distribution of the radiation (e.g., laser) power over the output arched surface 14. By uniform distribution, it is meant that an energy density (or power density) on a predetermined area (e.g., 3 mm$^2$) of the geometrical surface (e.g., arched surface 14) is within plus or minus about 5% of the average energy or power density of the geometrical surface (i.e., illuminated area). In another embodiments, the power density of a predetermined area (e.g., 3 mm$^2$) of the geometrical surface (e.g., arched surface 14) can be within plus or minus about 50% of the total average power density of the geometrical surface. In a modified embodiment, uniform distribution can mean that an energy density (or power density) on a predetermined area (e.g., 3 mm$^2$) of the geometrical surface (e.g., arched surface 14) is within plus or minus about 5% of that of an adjacent area of the same size. In contrast, the variance between a power density of a central area of a truncated fiber end output can be 200 to 1000% greater than the average power density of the total illuminated area.

Figure 3:
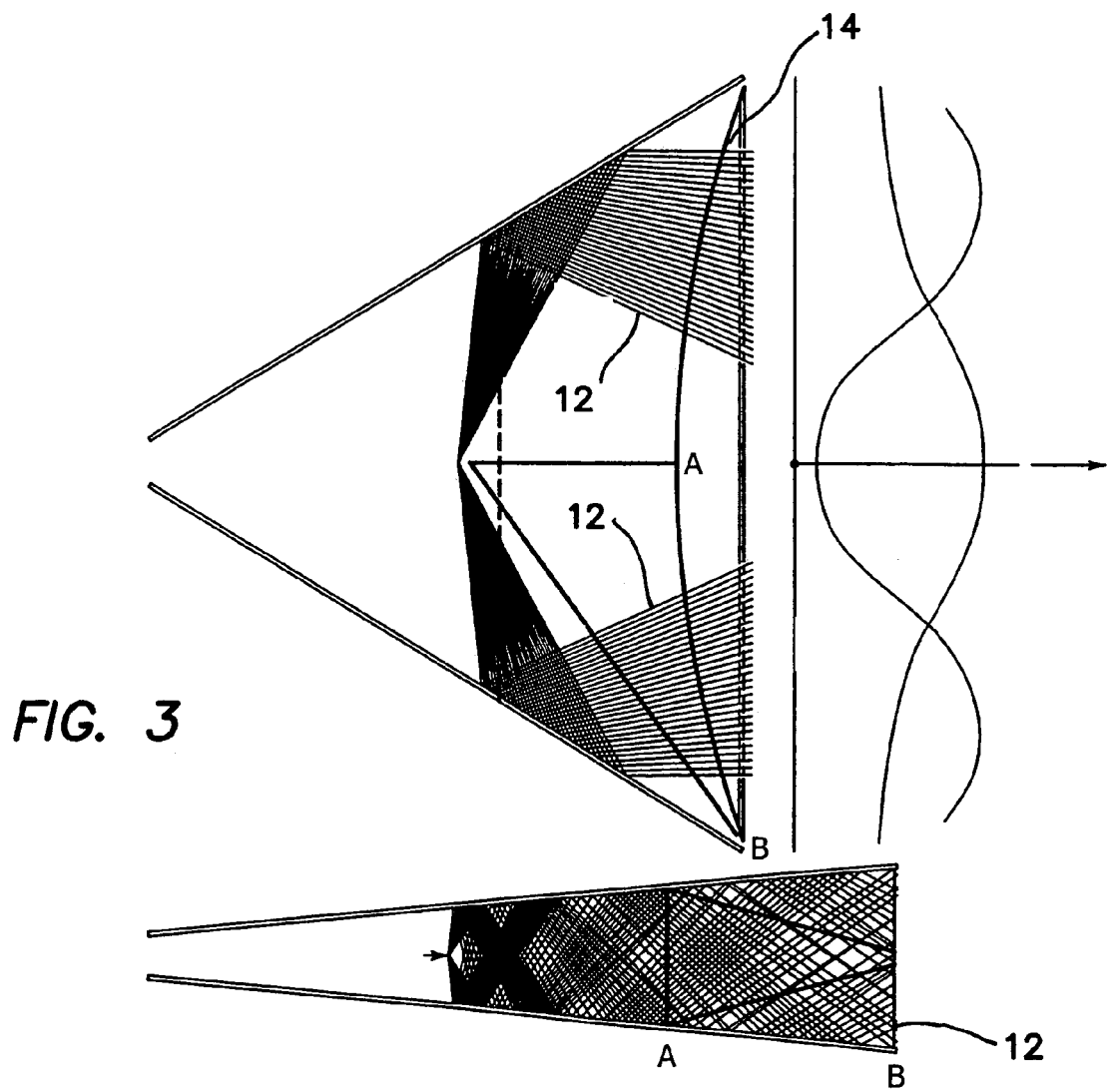
FIG. 3 shows two dimensional beam tracing diagrams of the optical scheme with the cone shaped fiber optic and tapered out trapezoidal mirror reflector.

With reference to FIG. 3, all beams of laser radiation exit from the fiber optic at high angles, up to 90 degrees to the fiber optic axis. As presently embodied, a dark "blind spot" is formed in front of the shaped fiber optic end 41. Yet another objective is to provide an apparatus for providing uniform distributions of power density across an illumination area, with optical losses less than 10% and/or with a minimal number of optical components.

With 61+/−1 degrees angle of the fiber optic cone (item 5 on FIG. 1) and 60+/−2 degrees angle of the tapered out mirror reflector (item 3), position of the fiber optic end was 17+/−1 mm from the output plane of the reflector's cone (FIG. 3). In this case, if consider reflections only from side mirrors, power distribution over the arched surface will have two maximums on the sides of the reflector. Top and bottom mirrors should be also tapered out at slight angle to have all laser beams eventually go out. Top and bottom mirrors (FIG. 3) were selected to form 10 degrees angle; in this case, distribution of the laser power over the arched surface (curved towards the light source) will have maximum in the middle. Superposition of those two distributions made overall power distributed very uniformly through the entire arched surface. A variation on the design of the handpiece may be so configured that it can direct EM/laser energy on the front, back or occlusal surfaces of the teeth.

To minimize losses of laser radiation, reflector should be made out of one piece. The material could be thermoconductive and thermoresistant and it could also have a good reflectivity for the wavelength or a reflective coating could be applied. The reflective coating could be, for example, gold, silver, copper, molybdenum, or diffusive reflectors such as ceramic, spectralon, berium sulphate or any other comparable materials. In one example, the material could be gold plated with R>96% for near IR radiation, 700 nm to 11000 nm). For some heat insulation, reflector is placed inside plastic handpiece funnel (item 2 on FIG. 1). To protect fiber optic end from damage, clear plastic window with anti-scratch coating is placed in front (item 9) and seals the mirror cavity.

The apparatus 10 may be used with a gel for whitening teeth, caries prevention, caries detection, and desensitizing teeth. The gel can comprise one or more of the following: (a) A target chromophore that could be a pigment, dye or chemical compound (Ultramarine Violet, Ultramarine Blue, '4301 Black', Caramel, or Black oxide), strongly absorbed by laser wavelengths in the infrared from 700 nm to 3 microns. (b) Furthermore, organic and inorganic pigments and dyes, and other food, drug and cosmetic color additives, which include, but are not limited to, the following: Complex inorganic odor pigments for shades of black, brown, red, yellow, green, blue and violet; Beta Carotene (orange/yellow); Riboflavin (orange/yellow); Iron oxides (black, brown, yellow and red); Ultramarines (green, blue, violet and red); Chromium oxide green; grape skin extract; dehydrated beets; and annalto extract (orange), can be implemented for activation by visible or infrared wavelengths. (c) Another type of additives are Epolight dyes for laser protective eyewear, which are disclosed in U.S. Provisional Application No. 60/314,858 and incorporated herein by reference and which can be implemented with the gel because of their specific selective absorption at the specific laser wavelength. (d) Agents to increase activation of the whitening substance such as metal powders (i.e. copper, bronze powder). (e) A whitening substance (including, but not limited to hydrogen peroxide or Carbamide peroxide) is capable of breaking down and removing stains in target material when activated by laser/EM energy directly, or via target chromophore absorption. (f) Substances for preventing or prohibiting caries development, such as Calcium fluoride, Amine fluoride, Sodium fluoride, Sodium monofluorophosphate, and Stannous fluoride are also considered as additives to the gel. The fluoride compound may also be used together with antibacterial agents capable of killing *Streptococcus sangius, Streptococcus mutans, Actinomyces viscosus*, and other bacteria associated with tooth caries. These agents may include benzol-konium chloride, phenol, stannous fluoride, sodium phenolate, sodium lauryl sulfate, sodium N-lauroyl sarcosinate, or sodium cocomonoglyceride sulfonate. (g) Another substance, Potassium nitrate, can be added to the gel for desensitizing effects on teeth.

The whitening substance could be hydrogen peroxide, carbamide peroxide or some other whitening substance, which could comprise up to 50% of the whitening gel. The pigment concentration can comprise up to 50% of the gel composition. In more specific embodiments, it comprises between 0.01% and 15% of the gel composition.

The following steps describe the method of using the whitening gel with the arched handpiece to whiten human teeth: (a) apply a layer of gel over the teeth surfaces; (b) place the handpiece above the gel-covered surfaces, on the upper or lower arch of the mouth; (c) activate the laser for the prescribed time duration; (d) wait for a predetermined period of time and activate the laser again if necessary.

In one embodiment, the laser is activated for 1-10 seconds. In another embodiment, the laser is activated for 10-30 seconds. In another embodiment, the laser is activated for 30-60 seconds. Laser activation times of over one minute could be applied depending on the type of stain and power density setting.

The waiting period between exposures may be from 0 seconds to 15 minutes in one embodiment, or between 15 and 30 minutes in another embodiment.

The laser power density may be, although not limited to, in the range of 0 W/cm$^2$-50 W/cm$^2$. In one embodiment, the power density is around 3 W/cm$^2$.

An example of a full-mouth procedure can be done by following these steps:
1) Divide the upper and lower arches of teeth into four quadrants, with each quadrant having up to 4 teeth or more.
2) Apply whitening gel to the teeth to be treated.
   2.1) Direct the whitening handpiece towards the first quadrant, using a laser power density of 3 W/cm$^2$.
   2.2) Activate the laser for 15 seconds, and then stop.
   2.3) Repeat the same procedure for the second, third and fourth quadrants.
   2.4) Wait for a period of ~1 minute and repeat steps 2.1-2.4 a further three to ten times depending on the condition of the patient's teeth.
   2.5) Remove the whitening gel from the teeth.
3) Repeat the treatment steps up to two more times depending on the nature of the patient's stain.

The above is just one example of a tooth whitening method using the whitening gel and handpiece. Time of exposure and number of applications can vary depending on the patient. Invention is not limited to the example procedure described above.

Laser energy in medicine is usually used as a surgical tool to remove tissue. Low Level Laser Therapy (LLLT) uses laser energy at power levels below those required to cut or ablate tissue, to nonthermally and nondestructively alter cellular function.

Nerve tissue, according to the literature, has a photosensitive component which reacts to laser exposure, reducing the excitability of the nerve cells by interrupting the fast pain fibers with a resultant reduction in pain. LLLT has also been shown to accelerate the repair process of crush-damaged nerves and improve function in both the CNS and peripheral nerves after injury.

The proposed delivery handpiece can be used to treat a number of symptoms and conditions, including: (a) pain reduction when directed at acupuncture points and muscular trigger points and when used to treat chronic tendinopathies, degenerative arthritis, rheumatoid arthritis, muscle pain, tendonitis tension myalgia, chronic radiculopathy, chronic neuropathy, acute soft tissue pain; also a reduction in tissue swelling, bruising and TMJ. (b) treatment of myofacial and postoperative pain; muscle tears; hematomas; tendonitis; shingles; herpes simplex; scarring; burn and wound healing According to this invention, the handpiece is designed in a shape and size broadly corresponding to the area to be treated, and will evenly distribute the energy over the target area. The electromagnetic wavelength for this device is between 0.4-11 nm. Typical power output levels for a treatment range from 10-700 mW, more specifically 15-100 mW. Energy levels range from 0-8 $J/cm^2$, more specifically 0-4 $J/cm^2$. Treatment time is between 10 seconds to 10 minutes, and more specifically 10 seconds to 4 minutes. Repeated treatments may be required on the same day and at different time intervals, or at different dates.

In a procedure utilizing this device, the clinician will point the handpiece towards either the tissue site requiring treatment, acupuncture points, or muscle trigger points, and then direct laser energy towards the target for a given period of time.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A laser handpiece, comprising;
a fiber optic end having a non-cylindrical shape; and
a reflector surrounding a portion of the fiber optic end and being shaped to direct laser energy emitted from the fiber optic end in a direction away from the laser handpiece and toward a treatment site, the reflector comprising a top reflector, a bottom reflector, and two side reflectors, and a spatial distribution of light emitted from the laser handpiece as a result of reflections from the side reflectors being relatively small along an optical axis of the fiber optic end.

2. The laser handpiece as set forth in claim 1, wherein a spatial distribution of light emitted from the laser handpiece as a result of reflections from the top and bottom reflectors is relatively large along the optical axis of the fiber optic end.

3. The laser handpiece as set forth in claim 2, wherein the fiber optic end has a conical shape.

4. The laser handpiece as set forth in claim 1, wherein the fiber optic end and the reflector together generate a resulting emitted radiation that has a relatively uniform power density across an area of a predetermined treatment site.

5. The laser handpiece as set forth in claim 4, wherein the area comprises a non-planar topography.

6. The laser handpiece as set forth in claim 1, wherein the non-cylindrical shape comprises tapered surfaces and is formed to facilitate total internal reflection of all waveguide modes on at least one of the tapered surfaces before exiting through the fiber optic end.

7. A laser handpiece, comprising:
a fiber optic end having a non-cylindrical shape; and
a reflector surrounding a portion of the fiber optic end and being shaped to direct laser energy emitted from the fiber optic end in a direction away from the laser handpiece and toward a treatment site, the reflector having a proximal end, a distal end, an optical axis extending from the proximal end to the distal end, and a width dimension measured in a direction perpendicular to the optical axis, a width dimension of the reflector at the distal end being greater than a width dimension of the reflector at the proximal end.

8. The laser handpiece as set forth in claim 7, wherein:
the fiber optic end has an optical axis; and
the fiber optic end is configured to output substantially all light in directions that are not parallel to the optical axis.

9. The laser handpiece as set forth in claim 7, wherein:
the fiber optic end has an optical axis; and
the fiber optic end is configured to output substantially all light in directions other than along the optical axis.

10. The laser handpiece as set forth in claim 7, wherein;
the fiber optic end has an optical axis; and
the fiber optic end is configured not to output light along the optical axis.

11. The laser handpiece as set forth in claim 7, wherein the non-cylindrical shape comprises tapered surfaces and is formed to facilitate total internal reflection of all waveguide modes on at least one of the tapered surfaces before exiting through the fiber optic end.

* * * * *